(12) United States Patent
Nagai et al.

(10) Patent No.: US 9,429,509 B2
(45) Date of Patent: Aug. 30, 2016

(54) PARTICLE ANALYZER AND PARTICLE ANALYSIS METHOD

(75) Inventors: Takaaki Nagai, Kobe (JP); Kazuhiro Yamada, Kobe (JP); Hiroaki Tobimatsu, Kobe (JP)

(73) Assignee: SYSMEX CORPORATION, Kobe (JP)

(*) Notice: Subject to any disclaimer, the term of this patent is extended or adjusted under 35 U.S.C. 154(b) by 1708 days.

(21) Appl. No.: 10/352,485

(22) Filed: Jan. 27, 2003

(65) Prior Publication Data

US 2003/0143117 A1    Jul. 31, 2003

(30) Foreign Application Priority Data

Jan. 28, 2002 (JP) ................................ 2002-018837

(51) Int. Cl.
| | | |
|---|---|---|
| G01N 33/49 | (2006.01) | |
| G01N 15/14 | (2006.01) | |
| G01N 33/00 | (2006.01) | |
| G01N 15/10 | (2006.01) | |

(52) U.S. Cl.
CPC .......... *G01N 15/1459* (2013.01); *G01N 33/49* (2013.01); *G01N 2015/1006* (2013.01); *G01N 2015/1402* (2013.01); *G01N 2015/1477* (2013.01); *G01N 2015/1486* (2013.01); *G01N 2015/1488* (2013.01)

(58) Field of Classification Search
CPC ..................... G01N 33/49; G01N 2015/1477; G01N 2015/1486; G01N 15/1459; G01N 2015/1006; G01N 2015/1402; G01N 2015/1488
USPC ............................................ 422/73; 436/63
See application file for complete search history.

(56) References Cited

U.S. PATENT DOCUMENTS

| | | | | |
|---|---|---|---|---|
| 3,646,313 | A * | 2/1972 | Gorgone et al. .............. 219/200 |
| 5,466,416 | A * | 11/1995 | Ghaed et al. .................... 422/52 |
| 5,679,575 | A * | 10/1997 | Kubota et al. ................... 436/49 |
| 5,691,486 | A * | 11/1997 | Behringer et al. ......... 73/863.73 |
| 5,731,867 | A * | 3/1998 | Katayama ........................ 356/73 |
| 6,200,531 | B1 * | 3/2001 | Liljestrand et al. ............. 422/52 |
| 6,369,893 | B1 * | 4/2002 | Christel et al. ................ 356/417 |
| 6,444,474 | B1 * | 9/2002 | Thomas et al. ................ 436/146 |
| 6,592,822 | B1 * | 7/2003 | Chandler ................... 422/82.05 |
| 6,764,215 | B2 * | 7/2004 | Meyler et al. .................. 374/32 |
| 2001/0000403 | A1 * | 4/2001 | Gaisford et al. .............. 219/748 |

FOREIGN PATENT DOCUMENTS

| | | |
|---|---|---|
| JP | 6-201585 A | 7/1994 |
| JP | 2001-74749 A | 3/2001 |
| WO | WO 01/12854 A2 | 2/2001 |

OTHER PUBLICATIONS

Thermometrics, "Thermometrics: What is a Thermistor?", www.thermometrics.com/htmldocs/whatis.htm, Feb. 19, 1999.*
Office Action for Japanese Patent Application 2003-016530, dated Oct. 24, 2006.

* cited by examiner

*Primary Examiner* — Rebecca M Fritchman
(74) *Attorney, Agent, or Firm* — Brinks Gilson & Lione

(57) ABSTRACT

Particle analyzers are described that include a cell for receiving a particles-containing liquid; a light source for irradiating light onto the particles-containing liquid; a photo-detector for detecting optical information from particles in the particles-containing liquid and converting the optical information into an electric signal; a temperature sensor for detecting a temperature of the particles-containing liquid; and a signal processing section for calculating an analysis result of the particles on the basis of an output of the photo-detector and an output of the temperature sensor. Particle analysis methods are also described.

25 Claims, 9 Drawing Sheets

PARTICLE ANALYZER AND PARTICLE ANALYSIS METHOD

RELATED APPLICATIONS

This application claims priority under 35 U.S.C. §119 to Japanese Patent Application No. 2002-018837, filed Jan. 28, 2002.

BACKGROUND

The present invention relates to a particle analyzer and a particle analysis method and, more particularly, to the analysis of cells and other formed components contained in blood or urine.

Chemiluminescence detection apparatuses have been described, wherein a photodetector detects the intensity of chemiluminescence occurring in a reaction cell. The apparatus is characterized in that a temperature sensor is provided in the vicinity of the reaction cell, and the intensity of chemiluminescence is thereby corrected on the basis of the temperature obtained by the temperature sensor (for example, Japanese Unexamined Patent Publication No. H6-201585).

Another example is an automatic analysis apparatus for detecting a chemical reaction by using a final reaction detection reagent such as a luminescent reagent. The apparatus includes a temperature measuring means for measuring the temperature of the final reaction detection reagent solution and a correcting means for correcting a final detection value on the basis of the measured temperature of the final reaction detection reagent solution (for example, Japanese Unexamined Patent Publication No. 2001-74749).

An example of a particle analyzer for analyzing particles, such as cells and blood cells in a sample liquid, is a flow cytometer using a sheath flow scheme. According to this scheme, sheath liquid flows around a particles-containing liquid ejected from a nozzle, and thereby forms sample liquid. In this scheme, the flow of the particles-containing liquid is narrowed hydrodynamically in the sheath flow cell. An optical measurement is performed at this site, whereby the particles in the particles-containing liquid are measured and analyzed.

The term "sheath flow" indicates a flow (e.g., of sample liquid) in which particles-containing liquid is narrowed substantially to the diameter of a particle, in the center part of sheath liquid flowing through an orifice in a laminar flow state, in which the particles accordingly pass through the orifice aligned in one line. Sample liquid prepared from a sample such as blood with a stain liquid, a hemolyzing agent, a reaction reagent, or the like is introduced into a flow cytometer, whereby various cells are analyzed.

In the above-mentioned optical measurement, the sample liquid is irradiated with light, whereby light generated from the particles in the sample liquid by the irradiated light is received by a photo-detector, and thereby converted into an electric signal. The electric signal is amplified by an amplifying section, and then the particles are analyzed on the basis of the electric signal.

Nevertheless, when the temperature of the sample liquid changes, the intensity of light from the particles also changes. This adversely affects the analysis result. Thus, a problem has resulted in that the sample liquid needs to be managed strictly at a predetermined temperature by using a incubator or the like.

SUMMARY

The scope of the present invention is defined solely by the appended claims, and is not affected to any degree by the statements within this summary.

The invention provides a particle analyzer, wherein the temperature of particles-containing liquid is detected, whereby correction is performed on the basis of the detected temperature, and whereby strict temperature control of the particles-containing liquid is unnecessary.

In a first aspect, the invention provides a particle analyzer comprising: a cell for receiving particles-containing liquid; a light source for irradiating light onto the particles-containing liquid; a photo-detector for detecting optical information from particles in the particles-containing liquid and then converting it into an electric signal; a temperature sensor for detecting the temperature, of the particles-containing liquid; and a signal processing section for calculating an analysis result of the particles on the basis of the output of the photo-detector and the output of the temperature sensor.

In a second aspect, the invention provides a particle analyzer comprising: a cell for receiving particles-containing liquid; a light source for irradiating light onto the particles-containing liquid; a photo-detector for detecting optical information from particles in the particles-containing liquid and then converting it into an electric signal; a temperature sensor for detecting the temperature of the particles-containing liquid; an analyzing section for processing and analyzing the electric signal; and a controlling section for receiving the output of the temperature sensor and thereby correcting the electric signal obtained by the photo-detector or the analysis result obtained by the analyzing section.

In a third aspect, the invention provides a particle analysis method comprising: introducing particles-containing liquid into a cell; irradiating the particles-containing liquid in the cell with light; detecting optical information from particles in the particles-containing liquid irradiated with light and then converting it into an electric signal; detecting the temperature of the particles-containing liquid; amplifying the electric signal on the basis of the temperature of the particles-containing liquid; and processing the amplified electric signal and thereby analyzing the particles.

DETAILED DESCRIPTION OF THE PRESENTLY PREFERRED EMBODIMENTS

Figure 1:
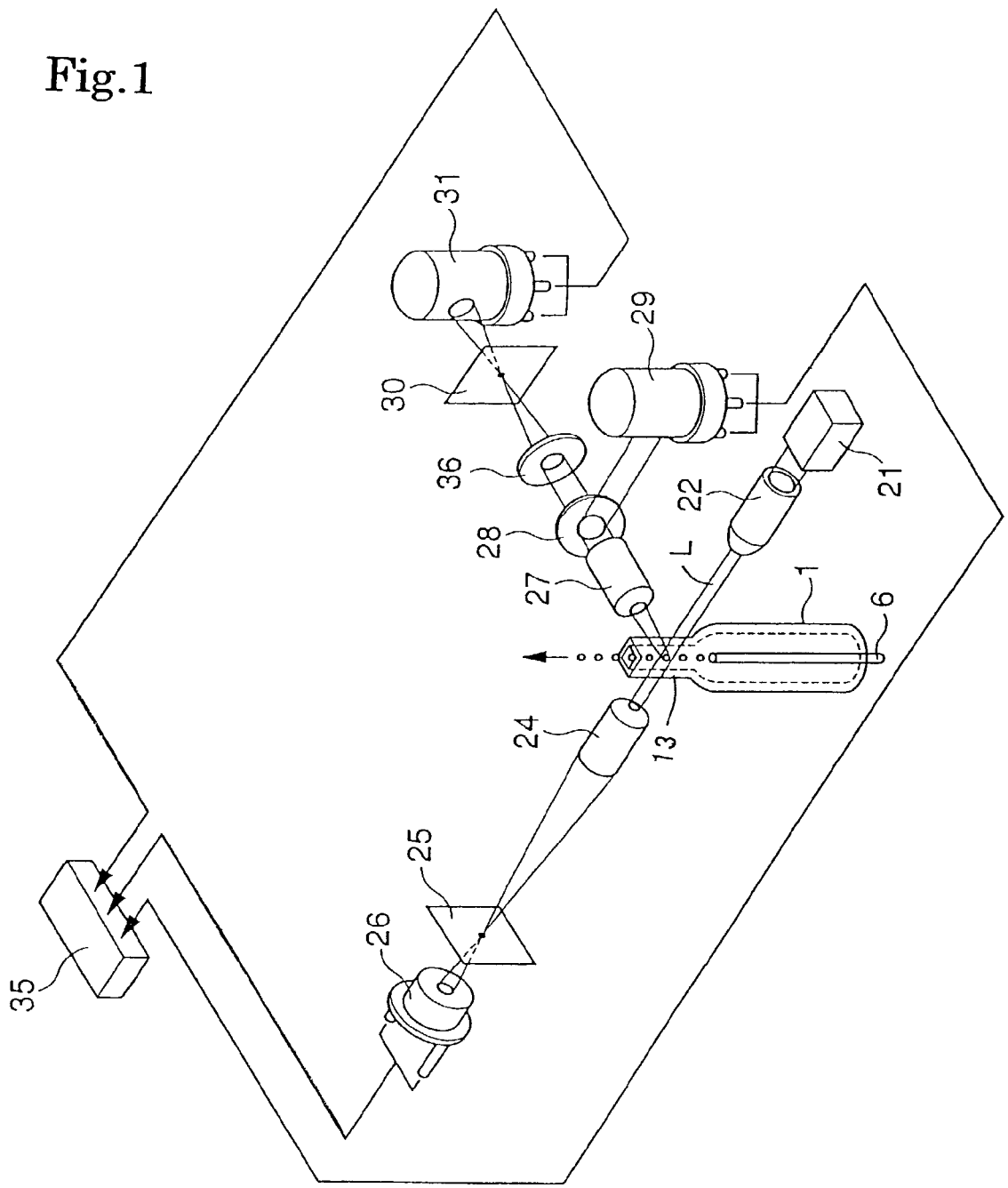
FIG. 1 is a perspective view of the configuration of a flow cytometer in accordance with the present invention.

The invention is described below in detail with reference to the embodiments illustrated in the drawings. Common elements to respective drawings are designated by common reference numerals. A flow cytometer is described below as an example of a particle analyzer. The following detailed description and accompanying drawings have been provided by way of explanation and illustration, and are not intended to limit the scope of the appended claims or their equivalents.

[Optical System of Flow Cytometer]

FIG. 1 is a perspective view of an optical system of a flow cytometer (a flow cytometer used in a hematology analyzer) according to an embodiment of the invention. In the figure, a beam emitted from a laser diode 21 is irradiated through a collimator lens 22 onto a sheath flow cell 1. Forward scattered light emitted from blood cells passing through the sheath flow cell 1 is made incident through a condenser lens 24 and a pinhole plate 25 on a photodiode 26.

As for side scattered light and side fluorescent light emitted from the blood cells passing through the sheath flow cell 1, the side scattered light is made incident through a condenser lens 27 and a dichroic mirror 28 on a photomultiplier tube 29. The side fluorescent light is made incident through the condenser lens 27, the dichroic mirror 28, a filter 36, and a pinhole plate 30 on a photomultiplier tube 31.

A forward scattered light signal outputted from the photodiode 26, a side scattered light signal outputted from the photomultiplier tube 29, and a side fluorescent light signal outputted from the photomultiplier tube 31 are inputted to a signal processing section 35.

[Fluid System of Flow Cytometer and Its Measurement and Washing Processes]

Figure 2:
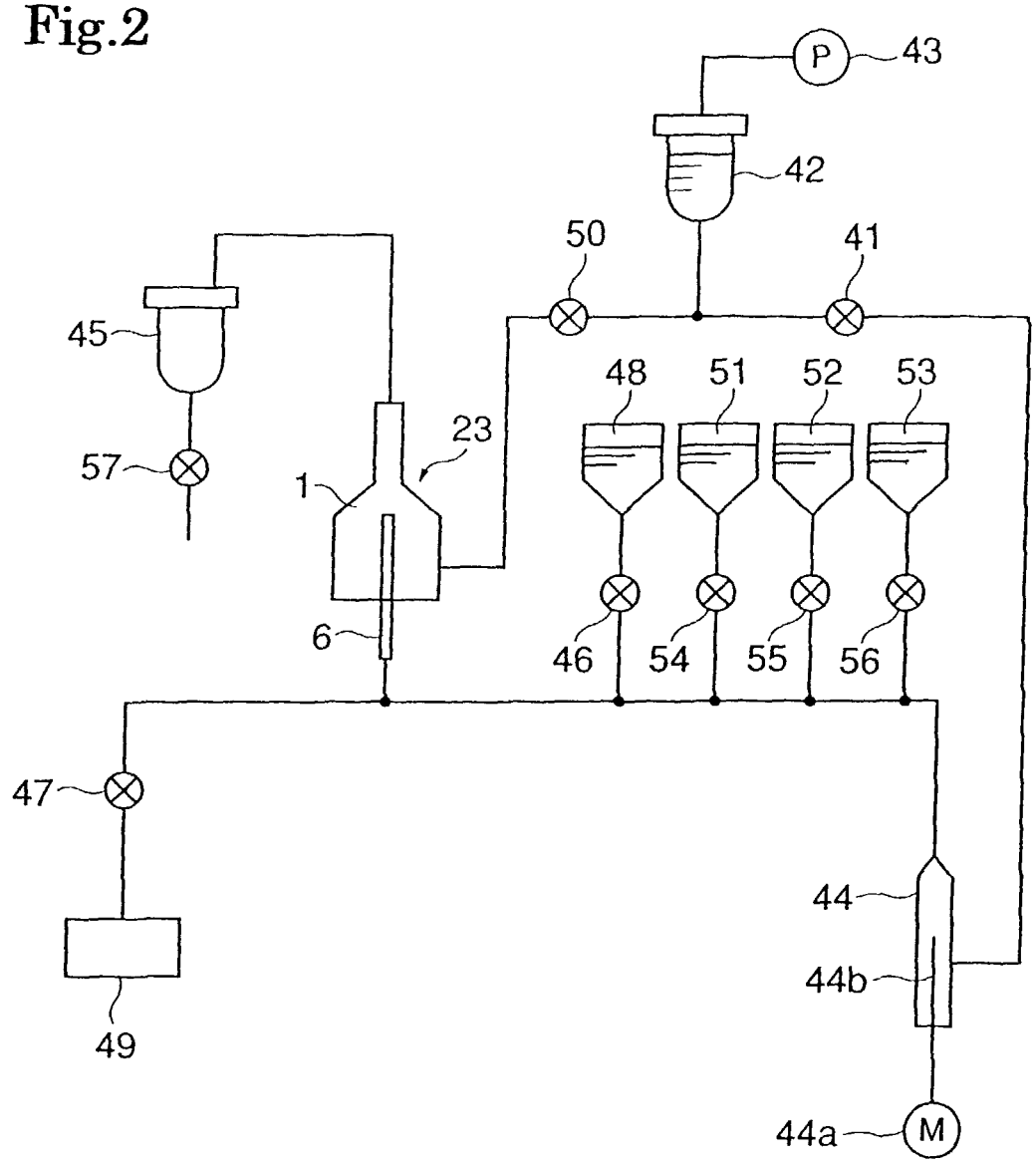
FIG. 2 is a system diagram showing a fluid system of a flow cytometer in accordance with the present invention.

FIG. 2 is a system diagram showing a fluid system of the flow cytometer shown in FIG. 1. Respective parts are connected with tubes. Valves are closed normally. In the figure, initially, in a washing process, valves 41 and 50 are opened, whereby sheath liquid is discharged from a sheath liquid chamber 42 containing the sheath liquid, by a pressure P generated by a pressure apparatus 43. The sheath liquid flows through the valve 41, a metering syringe 44, and a nozzle 6, and is then discharged into a waste fluid chamber 45. At the same time, the sheath liquid flows through the valve 50 and the sheath flow cell 1, and is then discharged into the waste fluid chamber 45. The valves 41 and 50 are closed after a predetermined time. As a result, the metering syringe 44, the nozzle 6, the sheath flow cell 1, and the paths thereof are washed with the sheath liquid.

Next, in a measurement process, valves 46 and 47 are opened, whereby particles-containing liquid is suctioned from a reaction chamber 48 containing blood-containing liquid (particles-containing liquid) reacted with a reagent, by negative pressure of a suction apparatus 49. When the path between the valve 46 and the nozzle 6 is filled with the particles-containing liquid, the valves 46 and 47 are closed. Then, the valve 50 is opened, whereby the sheath liquid is discharged from the sheath liquid chamber 42 to the sheath flow cell 1 by pressure of the pressure apparatus 43, and then discharged into the waste fluid chamber 45.

Then, the valve 41 is opened, whereby the pressure P of the pressure apparatus 43 is also transferred through the metering syringe 44 to the tip of the nozzle 6. As a result, at the tip of the nozzle 6, the pressure of the sheath liquid outside the nozzle and the pressure of the particles-containing liquid inside the nozzle reach an equilibrium. Accordingly, in this state, when a piston 44b of the metering syringe 44 is driven in the direction of discharging by a motor 44a, the particles-containing liquid located between the valve 46 and the nozzle 6 is easily discharged, and thereby narrowed and formed into sample liquid by the sheath liquid. The sample liquid flows through the sheath flow cell 1, and is then discharged into the waste fluid chamber 45. During this time, an optical measurement is performed on the sample liquid.

On completion of the driving of the piston 44b of the metering syringe 44, the measurement process is terminated. Then, the motor 44a rotates in reverse, and thereby pulls the piston 44b back in the direction of suction, whereby the metering syringe 44 is restored to its initial state. During this process, the valves 41 and 50 are maintained to be open. Accordingly, the above-mentioned washing process is performed, whereby the next measurement process is prepared.

Accordingly, the other particles-containing liquid contained in the other reaction chambers 51, 52, and 53 can also be measured by opening valves 54, 55, and 56 and successively performing processes similar to those described above.

A valve 57 is a valve for discharging the waste fluid from the waste fluid chamber 45, and opened when necessary.

[Optical Information Processing of Flow Cytometer]

Figure 3:
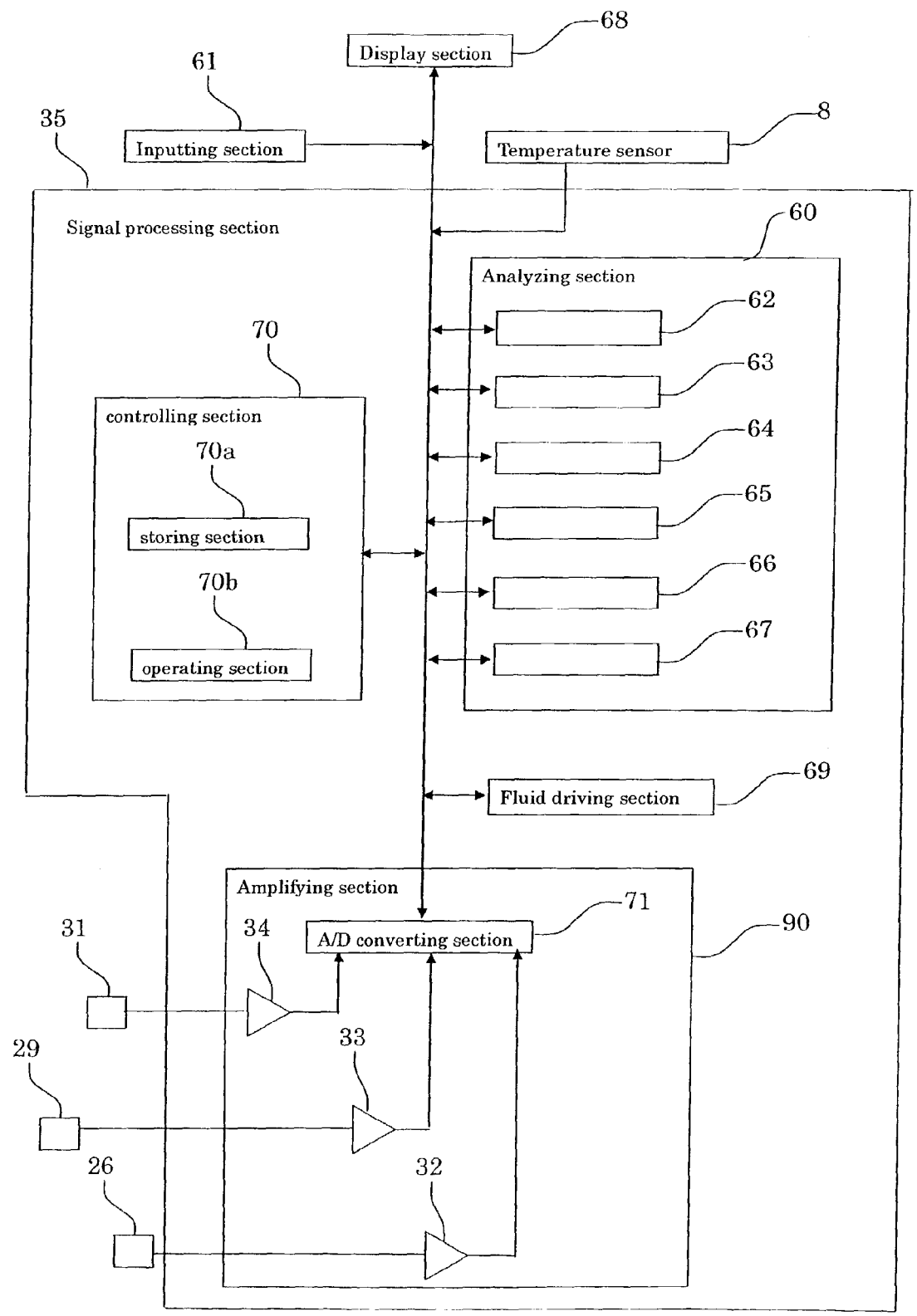
FIG. 3 is a block diagram showing mainly a signal processing section of a flow cytometer in accordance with the present invention.

FIG. 3 is a block diagram mainly showing the configuration of the signal processing section 35 shown in FIG. 1. As shown in FIG. 3, the signal processing section 35 comprises an analyzing section 60, a fluid driving section 69, a controlling section 70, and an amplifying section 90. The analyzing section 60 comprises a setting condition storing section 62, a data storing section 63, a distribution diagram generating section 64, an extracting section 65, a fraction region determining section 66, and an operation section 67.

The amplifying section 90 comprises an A/D converting section 71 and amplifiers 32, 33, and 34. The A/D converting section 71 A/D-converts signals amplified by the amplifiers 32, 33, and 34, that is, optical information having been converted into electric signals and then amplified, and then inputs it to the analyzing section 60.

An inputting section 61 is composed of, for example, a keyboard and a mouse for setting conditions, such as various numbers and regions, in advance.

The setting condition storing section 62 stores the various conditions having been set. The data storing section 63 stores the A/D-converted optical information. The distribution diagram generating section 64 generates a two-dimensional distribution diagram using any two parameters selected from the group consisting of forward scattered light intensity (Fsc), side scattered light intensity (Ssc), and side fluorescent light intensity (Sfl), which are pieces of optical information stored in the storing section 63. The extracting section 65 extracts coordinates and regions from the distribution diagram generated by the distribution diagram generating section 64.

The fraction region determining section 66 determines fraction regions for the particles in the distribution diagram generated by the distribution diagram generating section 64. The operation section 67 performs particle counting within the fraction region. The operation result from the operation section 67, together with the distribution diagram generated by the distribution diagram generating section 64, is displayed in a display section 68.

The fluid driving section 69 drives the valves 41, 46, 47, 50, 54, 55, 56, 57 and the motor 44a shown in FIG. 2. The analyzing section 60 and the controlling section 70 are integrally composed of a CPU, a ROM, a RAM, and the like.

[Blood Cell Measurement in Various Measurement Modes]

In the inputting section 61, anyone of the four measurement modes of "nucleated erythrocyte measurement mode", "leucocyte basophile measurement mode", "leucocyte four-classification measurement mode", and "reticulocyte measurement mode" is set for each specimen. Correspondingly to the setting, blood-metered by a blood metering section (not shown) and reagents such as a diluent, a stain liquid, and a hemolyzing agent are transferred into a corresponding chamber among the reaction chambers 48, 51, 52, and 53 shown in FIG. 2, whereby predetermined processes are performed. The blood-containing liquid prepared as described above is measured successively as follows.

In the "nucleated erythrocyte measurement mode", 18 µl of blood, together with 882 µl of Stromatolyser NR Hemolyzing agent (available from Sysmex Corporation), is transferred into the reaction chamber 48. Then, 18 µl of Stromatolyser NR Stain liquid (available from Sysmex Corporation) is added. The reaction is maintained for approximately 7 seconds in this state, whereby erythrocytes are hemolyzed, while leucocytes and nucleated erythrocytes are stained.

Figure 4:
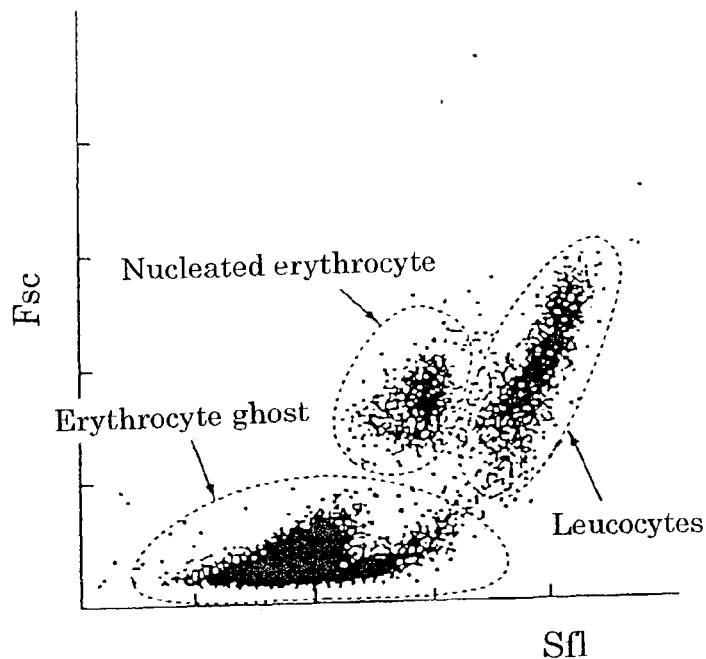
FIG. 4 is an example of a distribution diagram in accordance with the present invention.

The particles-containing liquid processed as described above is discharged from the nozzle 6 by the metering syringe 44, and thereby measured optically. FIG. 4 is an example of a two-dimensional distribution diagram with respect to the side fluorescent light (Sfl) and the forward scattered light (Fsc) among the information obtained by this measurement. Nucleated erythrocytes are fractioned from erythrocytes and leucocytes, and thereby measured.

In the "leucocyte basophile measurement mode", 18 µl of blood, together with 882 µl of Stromatolyser FB(II) (available from Sysmex Corporation), is transferred into the reaction chamber 51 shown in FIG. 2. The reaction is maintained for approximately 14 seconds in this state, whereby erythrocytes are hemolyzed, while leucocytes other than basophiles are denucleated and contracted.

Figure 5:
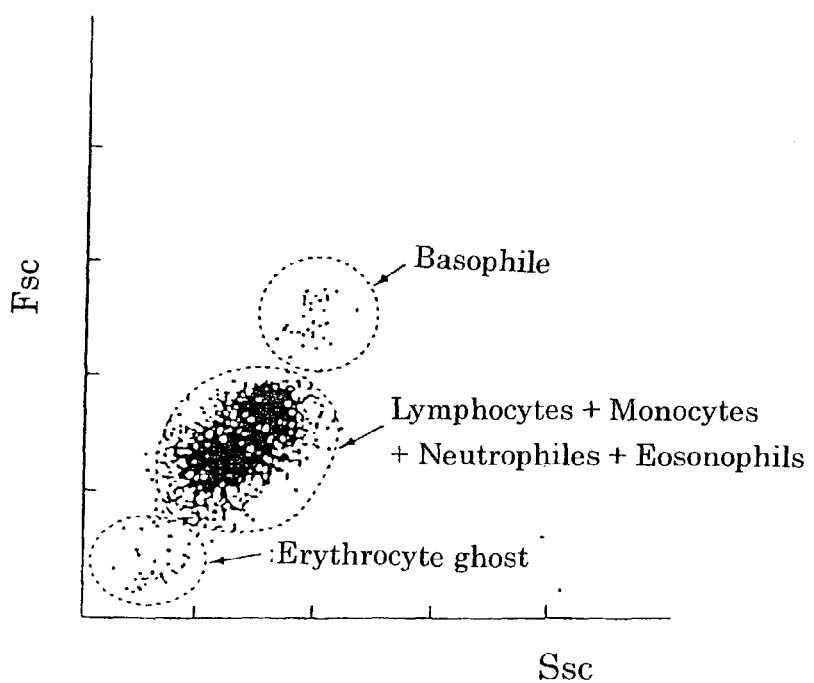
FIG. 5 is an example of a distribution diagram in accordance with the present invention.

The particles-containing liquid processed as described above is discharged from the nozzle 6 by the metering syringe 44, and thereby measured optically. FIG. 5 is an example of a two-dimensional distribution diagram with respect to the side scattered light (Ssc) and the forward scattered light (Fsc) among the information obtained by this measurement. Basophiles and leucocytes other than basophiles (lymphocytes+monocytes+neutrophiles+eosinophils) are fractioned and measured.

In the "leucocyte four-classification measurement mode", 18 µl of blood, together with 882 µl of Stromatolyser 4DL (available from Sysmex Corporation), is transferred into the reaction chamber 52 shown in FIG. 2. Then, 18 µl of Stromatolyser 4DS (available from Sysmex Corporation) is added. The reaction is maintained for approximately 22 seconds in this state, whereby erythrocytes are hemolyzed, while leucocytes are stained.

Figure 6:
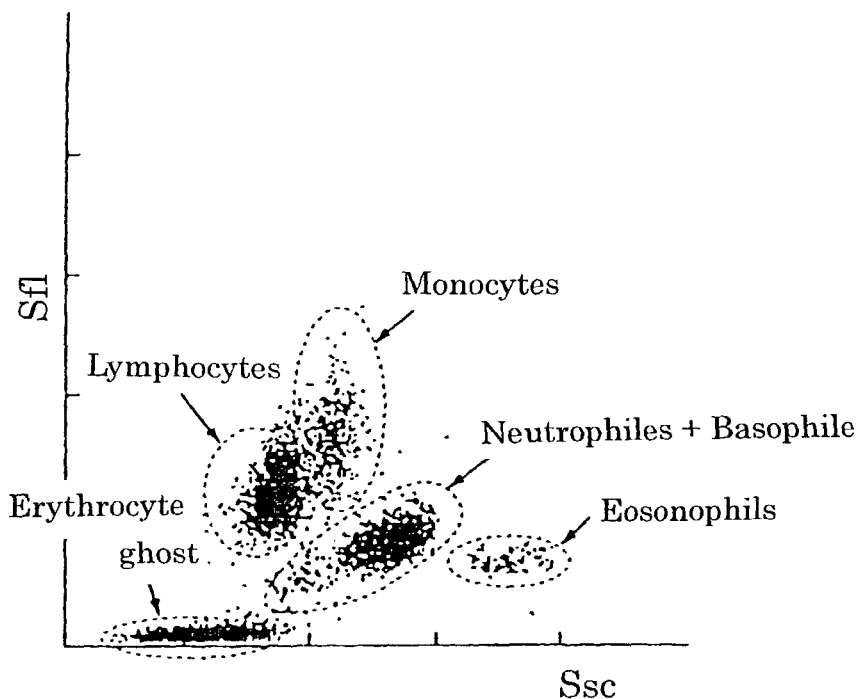
FIG. 6 is an example of a distribution diagram in accordance with the present invention.

The particles-containing liquid processed as described above is discharged from the nozzle 6 by the metering syringe 44, and thereby measured optically. FIG. 6 is an example of a two-dimensional distribution diagram with respect to the side scattered light (Ssc) and the side fluorescent light (Sfl) among the information obtained by this measurement. Leucocytes are fractioned into lymphocytes, monocytes, neutrophiles+basophiles, and eosinophils), and thereby measured.

In the "reticulocyte measurement mode", 4.5 µl of blood, together with 895.5 µl of Ret Search (II) Dilution Liquid (available from Sysmex Corporation), is transferred into the reaction chamber 53 shown in FIG. 2. Then, 18 µl of Ret Search (II) Stain liquid (available from Sysmex Corporation) is added. The reaction is maintained for 31 seconds in this state, whereby reticulocytes and the like are stained.

Figure 7:
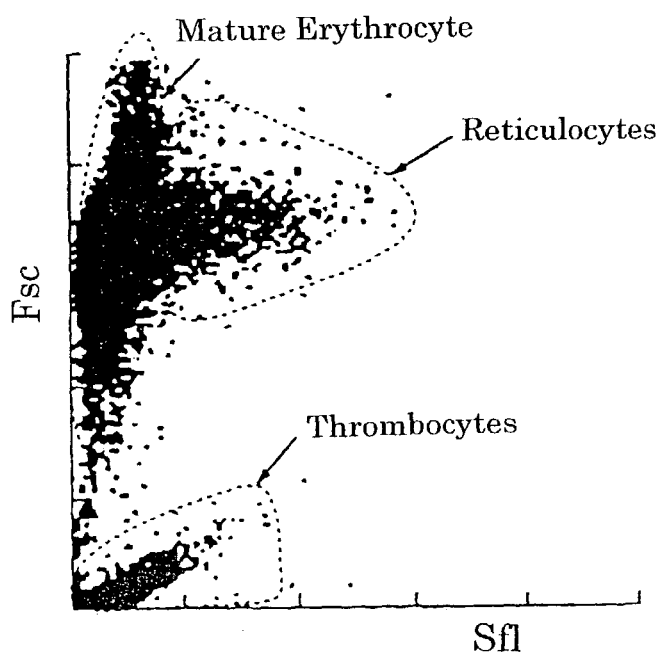
FIG. 7 is an example of a distribution diagram in accordance with the present invention.

The particles-containing liquid processed as described above is discharged from the nozzle 6 by the metering syringe 44, and thereby measured optically. FIG. 7 is an example of a two-dimensional distribution diagram with respect to the side fluorescent light (Sfl) and the forward scattered light (Fsc) among the information obtained by this measurement. Reticulocytes are fractioned from mature erythrocytes and thrombocytes, and thereby measured.

[Temperature Sensor of Sheath Flow Cell]

Figure 8:
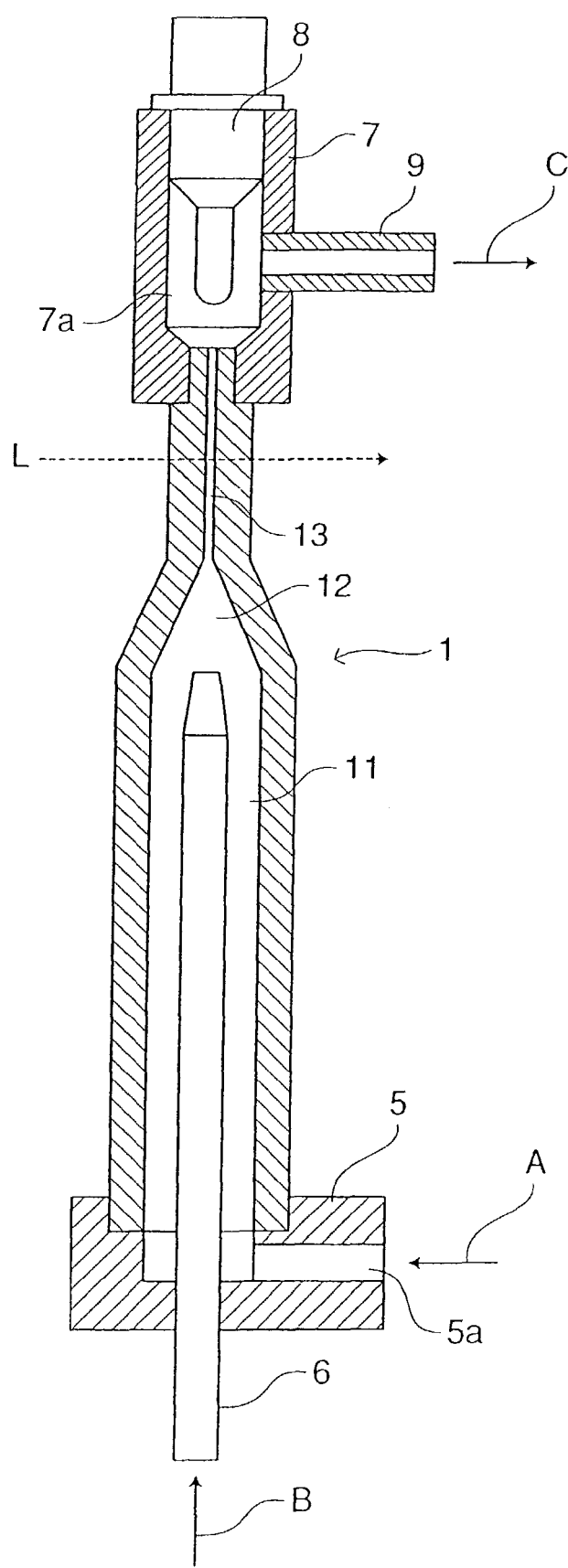
FIG. 8 is a vertical cross sectional view of a sheath flow cell in accordance with the present invention.

FIG. 8 is a cross sectional view of the sheath flow cell 1. The sheath flow cell 1 comprises a rectifying section 11, an accelerating section 12, and an orifice section 13.

The rectifying section 11 has a cylindrical through-hole, while the accelerating section 12 has a conical through-hole the diameter of which gradually decreases toward the orifice section 13.

Figure 9:
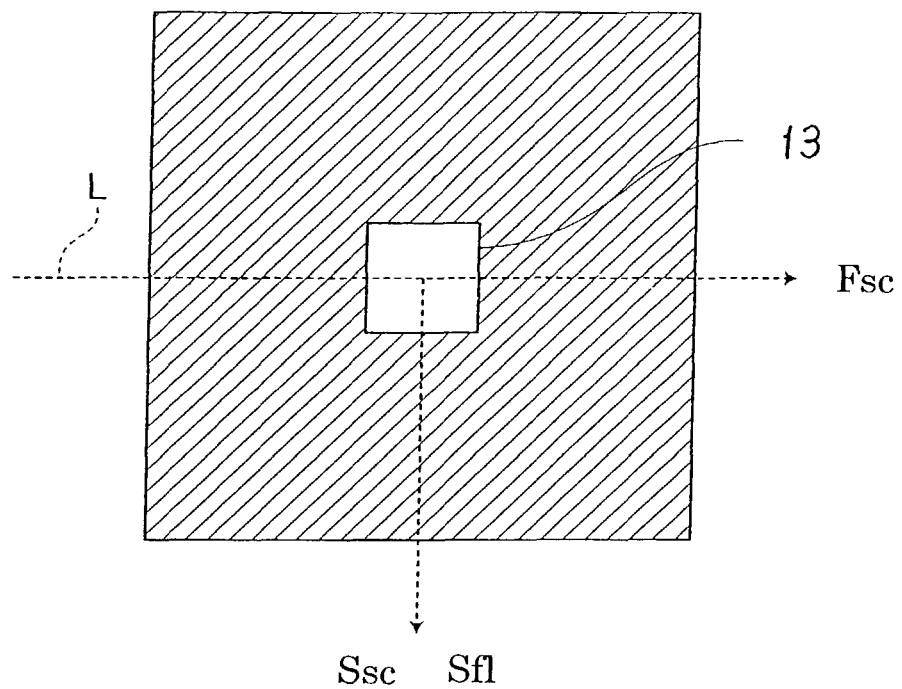
FIG. 9 is a horizontal cross sectional view of a sheath flow cell in accordance with the present invention.

The orifice section 13 of the sheath flow cell 1 is composed of a transparent rectangular tube having a square cross section so that particle measurement light L is irradiated, and that the forward scattered light (Fsc), the side scattered light (Ssc), and the side fluorescent light (Sfl) are measured as shown in FIG. 9.

As shown in FIG. 8, the sheath flow cell 1 is fixed by a fixing member 5, while the nozzle 6 is inserted into the sheath flow cell 1 such that the tip of the nozzle 6 reaches the boundary between the rectifying section 11 and the accelerating section 12. The nozzle 6 is then fixed to the fixing member 5 coaxially relative to the rectifying section 11.

On the other hand, at the outlet of the orifice section 13 of the sheath flow cell 1, a sensor arranging member 7 having a passage 7a is connected. The sensor arranging member 7 is provided with a temperature sensor 8 and a nipple 9, whereby the sample liquid introduced from the orifice section 13 into the passage 7a contacts with the temperature sensor 8, and is then discharged from the nipple 9. The temperature sensor 8 used herein includes a thermistor (Shibaura Electronics Co., Ltd., PB3M-35-TI).

As shown in FIG. 8, the sheath liquid introduced from the inlet 5a of the fixing member 5 is rectified by the rectifying section 11, and then accelerated by the accelerating section 12. The particles-containing liquid introduced into the nozzle 6 from the direction indicated by the arrow B is ejected from the tip of the nozzle 6 toward the orifice section 13, then surrounded by the accelerated sheath liquid, and thereby formed into the sample liquid passing through the orifice section 13. The sample liquid is irradiated with a beam L, whereby light generated by the particles in the sample liquid is detected by the photodiode 26 and the photomultiplier tubes 29 and 31 as shown in FIG. 1.

The temperature of the sample liquid having passed through the orifice section 13 is measured by the temperature sensor 8 in the sensor arranging member 7. After that, the sample liquid is discharged from the nipple 9 in the direction indicated by the arrow C.

As in this embodiment, the temperature sensor 8 may be arranged at the outlet of the sheath flow cell 1 so as to be exposed into the sample liquid. Alternatively, the temperature sensor 8 may be arranged at the inlet of the sheath flow cell 1 or its vicinity.

That is, the temperature sensor 8 may be arranged at any position where the detected temperature of the sample liquid is substantially the same as that of the sample liquid passing through the orifice section 13.

In case the amount of sheath liquid is substantially larger than that of the particles-containing liquid, the temperature of the particles-containing liquid may be substituted by the temperature of the sample liquid (mixture of the particles-containing liquid and the sheath liquid) or the sheath liquid. The situation is analogous for liquids other than the sheath liquid.

That is, in accordance with the present invention, the temperature of the particles-containing liquid indicates the temperature of the liquid in the cell, and may be the temperature of the sample liquid or the temperature of any liquid (such as the sheath liquid) used together with the particles-containing liquid. Further, the temperature of the particles-containing liquid may be measured outside the cell as long as the temperature is substantially the same as that of the liquid in the cell.

[Temperature Correction of Measured Values]

Figure 10:
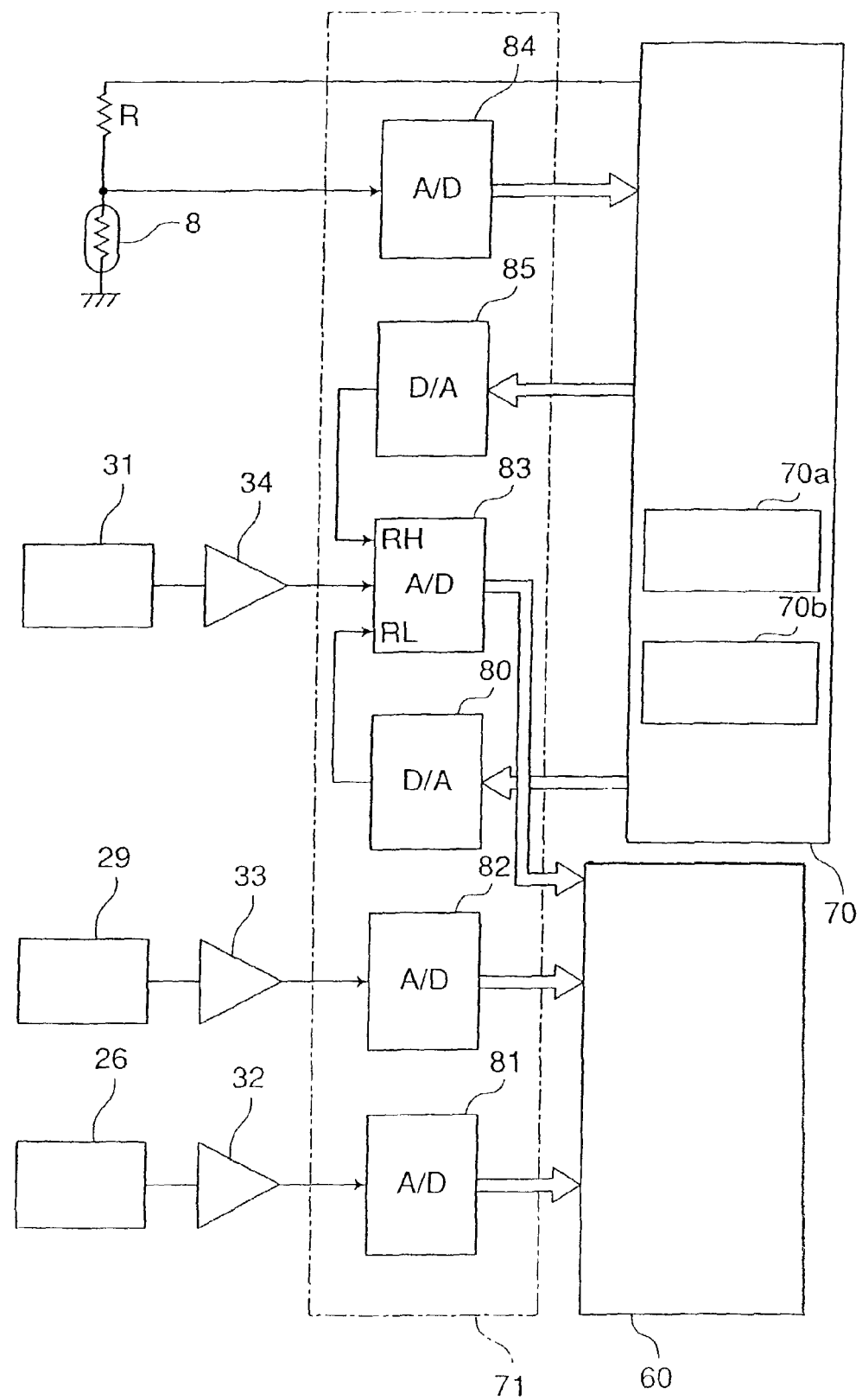
FIG. 10 is a detailed view of the main part of FIG. 3.

FIG. 10 is a detailed view of the main part of FIG. 3. An A/D converting section 71 comprises 10-bit A/D-converters 81, 82, 83 and 84 and 12-bit D/A converters 80 and 85. The A/D-converters 81, 82 and 83 A/D-convert the outputs of the amplifiers 32, 33 and 34, respectively, and then input them into the controlling section 70.

The temperature sensor 8, that is the thermistor, is supplied with a DC voltage from the controlling section 70 through a resistor R. The terminal voltage (temperature detection voltage) of the temperature sensor 8 is A/D-converted by the A/D converter 84, and then inputted into the controlling section 70.

The A/D converter 83 is provided with a constant voltage of 0.5 V serving as a low-level reference voltage RL from the controlling section 70 through the D/A converter 80. The A/D converter 83 is further provided with a control voltage serving as a high-level reference voltage RH from the controlling section 70.

Similarly, each of the A/D converters 81, 82 and 84 is provided with a constant low-level reference voltage and a high-level reference voltage (not shown) from the controlling section 70.

Figure 11:
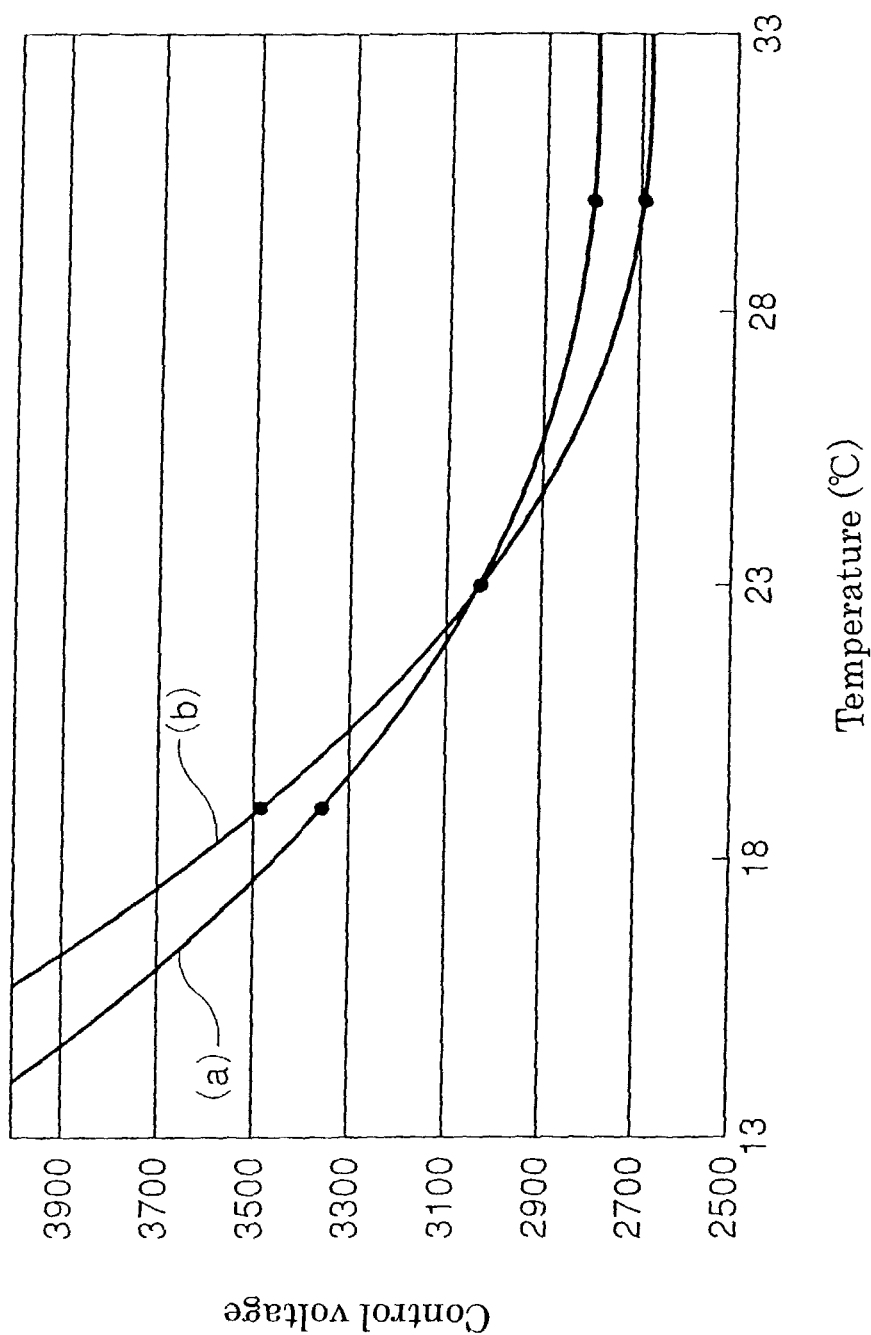
FIG. 11 is a graph showing the relation between the temperature and the control voltage in accordance with the present invention.

FIG. 11 shows correction curves (actually measured value) for the measured value of the side fluorescent light with respect to the temperature detected by the temperature sensor 8. The curve indicates the relation between the temperature (° C.) and the control voltage (12-bit digital value). The curve (a) corresponds to the case in which the reticulocytes are measured, while the curve (b) corresponds to the case of leucocytes and nucleated erythrocytes.

In FIG. 11, the horizontal axis is denoted by x, while the vertical axis is denoted by y. Further, the temperature of 23° C. is set to be the origin (0° C.). Then, the curves (a) and (b) are approximated respectively as follows.

$$y = 4.4838x^2 - 64.815x + 3031 \quad (A)$$

$$y = 5.7169x^2 - 88.919x + 3031 \quad (B)$$

These Formulas (A) and (B) are stored in a storing section 70a of the controlling section 70 in advance.

Then, in the above-mentioned "reticulocyte measurement mode", when the side fluorescent light (Sfl) is measured, the temperature of the sample liquid detected by the temperature sensor 8 is inputted through the A/D converter 84 to the controlling section 70.

In an operation section 70b of the controlling section 70, a corresponding control voltage (12-bit digital value) is derived according to Formula (A), and then inputted to the D/A converter 85. The D/A converter 85 converts the control voltage into an analog voltage, and then inputs it as the high-level reference voltage RH to the A/D converter 83. The A/D converter 83 converts the analog output voltage of the amplifier 34 into a digital value, and then inputs it to the analyzing section 60.

In the A/D converter 83, an input analog voltage between the high-level reference voltage RH and the low-level reference voltage RL is converted into a 10-bit digital value and then outputted. Accordingly, the ratio of the analog input to the digital output of the A/D converter 83, that is, the gain A, is determined by the difference (RH-RL) between RH and RL.

However, the low-level reference voltage RL is constant at 0.5 V. Accordingly, the gain A is controlled according to the high-level reference voltage RH, that is, the control voltage determined according to Formula (A), whereby the measured value of the side fluorescent light (Sfl) is corrected on the basis of the detected temperature from the temperature sensor 8.

In the above-mentioned "nucleated erythrocyte measurement mode" and "leucocyte four-classification measurement mode", when the side fluorescent light (Sfl) is measured, Formula (B) is used, whereby the measured value of the side fluorescent light (Sfl) is similarly corrected on the basis of the detected temperature from the temperature sensor 8.

As such, the measured value of the side fluorescent light, which varies depending on the temperature of the sample liquid, is corrected appropriately. This permits the flow cytometer to perform precision analysis at any time.

In accordance with this embodiment, the fluorescent light alone has been corrected. However, the forward scattered light and the side scattered light may also be corrected.

In accordance with this embodiment, the correction has been performed by amplifying the electric signal obtained by the photo-detector. However, on receiving the output of the temperature sensor, the analysis result obtained by the analyzing section may be corrected.

The detailed description provided above has referred to the case of a flow cytometer. However, the invention is not limited to this. For example, the invention is also applicable to a particle analyzer in which particles-containing liquid is introduced into a cell, and in which the particle size is calculated from the velocity of the Brownian motion of particles. The foregoing detailed description and accompanying drawings were provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A flow cytometer comprising:
   a flow cell comprising an outlet, wherein the flow cell is configured to:
   receive a cells-containing liquid and form a flow of the cells-containing liquid;
   surround the cells-containing liquid with a sheath liquid to form a sample liquid; and
   discharge the sample liquid at the outlet;

a light source that irradiates light onto the flow of the cells-containing liquid formed by the flow cell;

a photo-detector that detects optical information from cells in the flow of the cells-containing liquid and converts the optical information into an electric signal;

a temperature sensor configured to detect a temperature of the sample liquid, wherein the temperature sensor is arranged at the outlet of the flow cell such that the temperature sensor is configured to detect the temperature of the sample liquid after the flow of the cells-containing liquid is irradiated by the light source; and a signal processing section that comprises a processor that executes instructions encoded on a computer readable medium that classifies cells and measures the classified cells on the basis of an output of the photo-detector and an output of the temperature sensor.

2. The flow cytometer of claim 1, wherein the signal processing section interfaces: a temperature dependent variable amplifier that amplifies the electric signal, thereby producing an amplified electric signal; a controlling section for receiving the output of the temperature sensor and thereby controls the amplifier; and further comprises an analyzing section that executes instructions encoded on the computer readable medium for processing and analyzing the amplified electric signal.

3. The flow cytometer of claim 2, wherein: the temperature dependent variable amplifier comprises an A/D converter that converts an inputted analog signal into an outputted digital signal of predetermined bits; and the controlling section comprises the processor that executes instructions encoded on a computer readable medium that controls a ratio between the inputted analog signal and the outputted digital signal of the A/D converter.

4. The flow cytometer of claim 2, wherein the controlling section comprises a memory storing a relation formula for indicating an amplification factor corresponding to a temperature, and thereby controlling the amplifying section based on the relation formula.

5. The flow cytometer of claim 4, wherein the memory stores a plurality of relation formulae, each of which corresponds to classified cells to be measured.

6. The flow cytometer of claim 1, wherein the temperature sensor comprises a thermistor.

7. The flow cytometer of claim 1, wherein the flow cell comprises: a cell having an inlet, the outlet, and a through-hole communicating therebetween; and a nozzle inserted from the inlet into the through-hole coaxially, and wherein the sheath liquid is supplied from the inlet to the outlet of the cell, while the cells-containing liquid is supplied through the nozzle into the cell.

8. The flow cytometer of claim 1, wherein the light source comprises a laser light source, and irradiates light from the outside of the flow cell in a direction perpendicular to a flow of the sample liquid.

9. The flow cytometer of claim 1, wherein the optical information from the cells in the cells-containing liquid comprises information on luminescent light emitted from the cells excited by irradiated light from the light source.

10. The flow cytometer of claim 2, wherein the analyzing section processes the amplified electric signal, and thereby classifies the cells and counts the classified cells.

11. A flow cytometer comprising:

a flow cell for receiving a cells-containing liquid that forms a flow channel for the cells-containing liquid;

a light source for irradiating the flow of the cells-containing liquid within the flow channel;

a photo-detector optically linked to the flow channel that detects optical information from cells in the flow of the cells-containing liquid in the flow-channel and converts the optical information into an electric signal;

a temperature sensor arranged to receive the cells-containing liquid after the cells-containing liquid has been irradiated by the light source for detecting a temperature of the cells-containing liquid after irradiation; and a processor that executes instructions retained on a computer readable medium that:

analyzes the electric signal and thereby classifies the cells, and measures the classified cells as an analysis result; and corrects the electric signal obtained by the photo-detector or the analysis result obtained by the analysis of on an output of the temperature sensor.

12. The flow cytometer of claim 11, further comprising an amplifier for amplifying the electric signal obtained by the photo-detector, thereby producing an amplified electric signal, wherein a controlling section comprising the processor that executes instructions retained on a computer readable medium receives the output of the temperature sensor, controls the amplifier, and thereby corrects the electric signal obtained by the photo-detector.

13. The flow cytometer of claim 12, wherein: the amplifier comprises an A/D converter that converts an analog signal into a digital signal; and the controlling section controls a ratio between the analog signal and the digital signal.

14. The flow cytometer of claim 12, wherein the controlling section comprises a memory storing a relation formula for indicating an amplification factor corresponding to a temperature, and thereby controlling the amplifying section based on the relation formula.

15. The flow cytometer of claim 14, wherein the memory stores a plurality of relation formulae, each of which corresponds to the classified cells to be measured.

16. The flow cytometer of claim 11, wherein the flow cell receives the cells-containing liquid, surrounds the cells-containing liquid with a sheath liquid, and thereby forms and discharges a sample liquid.

17. The flow cytometer of claim 16, wherein the temperature sensor comprises a thermistor, and is arranged at an outlet of the flow cell so as to be exposed to the sample liquid.

18. The flow cytometer of claim 11, wherein the optical information from the cells in the cells-containing liquid comprises information on luminescent light emitted from the cells excited by irradiated light from the light source.

19. A flow cytometer comprising:

a flow cell for receiving a cells-containing liquid and for forming a flow of the cells-containing liquid;

a light source for irradiating the flow of the cells-containing liquid;

a photo-detector for detecting optical information from cells in the flow of the cells-containing liquid and for converting the optical information into an electric signal;

a temperature sensor positioned to detect a temperature of the cells-containing liquid after the cells-containing liquid is irradiated by the light source;

a variable gain amplifier that amplifies, based on the detected temperature, the electric signal, where the variable gain is based on the detected temperature; and an analyzing section that comprises a processor that executes instructions encoded on a computer readable medium that processes and analyzes the amplified electric signal and thereby classifies cells, and measures the classified cells based on the amplified electric signal.

20. The flow cytometer of claim 1, wherein the signal processing section classifies the cells into nucleated erythrocytes and other cells, and measures the classified nucleated erythrocytes.

21. The flow cytometer of claim 1, wherein the signal processing section classifies the cells into basophiles and other leucocytes and measures the classified basophiles.

22. The flow cytometer of claim 1, wherein the signal processing section classifies cells into lymphocytes, monocytes, neutrophiles, basophiles, and eosinophils and measures the classified lymphocytes, monocytes, neutrophiles, basophiles, and eosinophils.

23. The flow cytometer of claim 1, wherein the signal processing section classifies the cells into reticulocytes and other cells and measures the classified reticulocytes.

24. The flow cytometer of claim 1, wherein the optical information comprises scattered light and/or fluorescent light.

25. A flow cytometer comprising:

a flow cell configured to receive a cells-containing liquid and for forming a flow of the cells-containing liquid in a first direction;

a light source configured to irradiate light onto the flow of the cells-containing liquid formed by the flow cell;

a photo-detector configured to detect optical information from cells in the flow of the cells-containing liquid and for converting the optical information into an electric signal;

a temperature sensor configured to detect a temperature of the cells-containing liquid, wherein the temperature sensor is arranged at a position relative to the flow of the cells-containing liquid in the first direction that is after a position at which the cells-containing liquid is irradiated by the light source, wherein the position of the temperature sensor is such that the detected temperature of the cells-containing liquid is substantially the same as a temperature of the cells-containing liquid at a position where the cells-containing liquid is irradiated by the light source; and a signal processor that executes instructions retained in a computer readable medium that classifies cells on the basis of an output of the photo-detector and an output of the temperature sensor.

* * * * *